(12) United States Patent
Stirton et al.

(10) Patent No.: US 6,972,853 B1
(45) Date of Patent: Dec. 6, 2005

(54) METHODS OF CALIBRATING AND CONTROLLING STEPPER EXPOSURE PROCESSES AND TOOLS, AND SYSTEM FOR ACCOMPLISHING SAME

(75) Inventors: James Broc Stirton, Austin, TX (US); Homi E. Nariman, Austin, TX (US)

(73) Assignee: Advanced Micro Devices, Inc., Austin, TX (US)

( * ) Notice: Subject to any disclaimer, the term of this patent is extended or adjusted under 35 U.S.C. 154(b) by 383 days.

(21) Appl. No.: 10/259,044

(22) Filed: Sep. 27, 2002

(51) Int. Cl.[7] ............................. G01B 11/28; G03K 7/23
(52) U.S. Cl. ............................. 356/630; 430/30; 438/16
(58) Field of Search ............................. 356/603–604, 356/606–610, 620, 630–636, 392–394; 250/559.09, 250/559.16, 559.45, 225; 438/5–18, 695; 430/30

(56) References Cited

U.S. PATENT DOCUMENTS

| | | | | |
|---|---|---|---|---|
| 4,082,453 A | * | 4/1978 | Knop ............................. 355/88 |
| 5,164,790 A | * | 11/1992 | McNeil et al. ............... 356/496 |
| 5,300,786 A | * | 4/1994 | Brunner et al. ............. 250/548 |
| 5,867,276 A | | 2/1999 | McNeil et al. ............... 356/445 |
| 5,877,860 A | | 3/1999 | Borden ......................... 356/376 |
| 5,880,838 A | | 3/1999 | Marx et al. .................. 356/351 |
| 6,051,348 A | | 4/2000 | Marinaro et al. ............. 430/30 |
| 6,081,334 A | | 6/2000 | Grimbergen et al. ........ 356/357 |
| 6,245,584 B1 | | 6/2001 | Marinaro et al. ............. 438/14 |
| 6,433,878 B1 | * | 8/2002 | Niu et al. ..................... 356/603 |
| 6,479,200 B1 | * | 11/2002 | Stirton ........................ 430/30 |
| 6,639,663 B1 | * | 10/2003 | Markle et al. ........... 356/237.4 |
| 6,643,008 B1 | * | 11/2003 | Stirton et al. ............. 356/237.5 |

OTHER PUBLICATIONS

U.S Appl. No. 09/879,338, filed Jun. 11, 2001, Stirton et al.

* cited by examiner

*Primary Examiner*—Hoa Q. Pham
*Assistant Examiner*—Sang H. Nguyen
(74) *Attorney, Agent, or Firm*—Williams, Morgan & Amerson, P.C.

(57) ABSTRACT

The present invention is generally directed to various methods of stepper exposure processes and tools, and system for accomplishing same. In one embodiment, the method comprises forming a grating structure comprised of a plurality of photoresist features above a semiconducting substrate, measuring at least one characteristic of at least one of the photoresist features at a plurality of locations within the grating structure, and determining if the measured characteristic of the photoresist features varies across the grating structure.

51 Claims, 5 Drawing Sheets

METHODS OF CALIBRATING AND CONTROLLING STEPPER EXPOSURE PROCESSES AND TOOLS, AND SYSTEM FOR ACCOMPLISHING SAME

BACKGROUND OF THE INVENTION

1. Field of the Invention

This invention relates generally to semiconductor fabrication technology, and, more particularly, to methods of calibrating and controlling stepper exposure processes and tools, and system for accomplishing same.

2. Description of the Related Art

There is a constant drive within the semiconductor industry to increase the operating speed of integrated circuit devices, e.g., microprocessors, memory devices, and the like. This drive is fueled by consumer demands for computers and electronic devices that operate at increasingly greater speeds. This demand for increased speed has resulted in a continual reduction in the size of semiconductor devices, e.g., transistors. That is, many components of a typical field effect transistor (FET), e.g., channel length, junction depths, gate insulation thickness, and the like, are reduced. For example, all other things being equal, the smaller the channel length of the transistor, the faster the transistor will operate. Thus, there is a constant drive to reduce the size, or scale, of the components of a typical transistor to increase the overall speed of the transistor, as well as integrated circuit devices incorporating such transistors.

Figure 1:
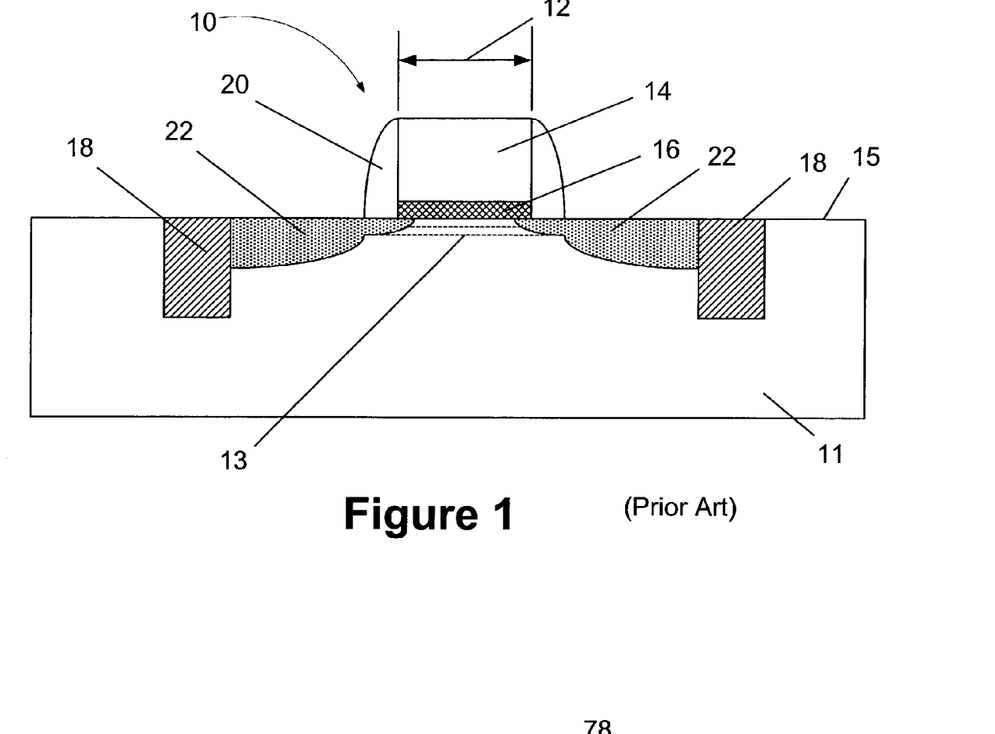
FIG. 1 is a cross-sectional view of an illustrative prior art transistor.

By way of background, an illustrative field effect transistor 10, as shown in FIG. 1, may be formed above a surface 15 of a semiconducting substrate or wafer 11 comprised of doped-silicon. The substrate 11 may be doped with either N-type or P-type dopant materials. The transistor 10 may have a doped polycrystalline silicon (polysilicon) gate electrode 14 formed above a gate insulation layer 16. The gate electrode 14 and the gate insulation layer 16 may be separated from doped source/drain regions 22 of the transistor 10 by a dielectric sidewall spacer 20. The source/drain regions 22 for the transistor 10 may be formed by performing one or more ion implantation processes to introduce dopant atoms, e.g., arsenic or phosphorous for NMOS devices, boron for PMOS devices, into the substrate 11. Shallow trench isolation regions 18 may be provided to isolate the transistor 10 electrically from neighboring semiconductor devices, such as other transistors (not shown). Additionally, although not depicted in FIG. 1, a typical integrated circuit device is comprised of a plurality of conductive interconnections, such as conductive lines and conductive contacts or vias, positioned in multiple layers of insulating material formed above the substrate. These conductive interconnections allow electrical signals to propagate between the transistors formed above the substrate.

The gate electrode 14 has a critical dimension 12, i.e., the width of the gate electrode 14, that approximately corresponds to the channel length 13 of the device when the transistor 10 is operational. Of course, the critical dimension 12 of the gate electrode 14 is but one example of a feature that must be formed very accurately in modern semiconductor manufacturing operations. Other examples include, but are not limited to, conductive lines, openings in insulating layers to allow subsequent formation of a conductive interconnection, i.e., a conductive line or contact, therein, etc.

In the process of forming integrated circuit devices, millions of transistors, such as the illustrative transistor 10 depicted in FIG. 1, are formed above a semiconducting substrate. In general, semiconductor manufacturing operations involve, among other things, the formation of layers of various materials, e.g., polysilicon, metals, insulating materials, etc., and the selective removal of portions of those layers by performing known photolithographic and etching techniques. These processes are continued until such time as the integrated circuit device is complete.

During the course of fabricating such integrated circuit devices, a variety of features, e.g., gate electrodes, conductive lines, openings in layers of insulating material, etc., are formed to very precisely controlled dimensions. Such dimensions are sometimes referred to as the critical dimension (CD) of the feature. It is very important in modern semiconductor processing that features be formed as accurately as possible due to the reduced size of those features in such modern devices. For example, gate electrodes may now be patterned to a width 12 that is approximately 0.13–0.18 μm (1300–1800 Å), and further reductions are planned in the future. As stated previously, the width 12 of the gate electrode 14 corresponds approximately to the channel length 13 of the transistor 10 when it is operational. Thus, even slight variations in the actual dimension of the feature as fabricated may adversely affect device performance. Thus, it is very important to accurately, reliably and repeatedly form features to their desired critical dimension, i.e., to form the gate electrode 14 to its desired critical dimension 12.

Photolithography is a process typically employed in semiconductor manufacturing. Photolithography generally involves forming a layer of photoresist material (positive or negative) above one or more layers of material, e.g., polysilicon, silicon dioxide, that are desired to be patterned. Thereafter, a pattern that is desired to be formed in the underlying layer or layers of material is initially formed in the layer of photoresist using an appropriate stepper tool and known photolithographic techniques, i.e., an image on a reticle in the stepper tool is transferred to the layer of photoresist. Then, the layer of photoresist is developed so as to leave in place a patterned layer of photoresist substantially corresponding to the pattern on the reticle. This patterned layer of photoresist is then used as a mask in subsequent etching processes, wet or dry, performed on the underlying layer or layers of material, e.g., a layer of polysilicon, metal or insulating material, to transfer the desired pattern to the underlying layer. The patterned layer of photoresist is comprised of a plurality of photoresist features, e.g., line-type features or opening-type features, that are to be replicated in an underlying process layer. The features in the patterned layer of photoresist also have a critical dimension, sometimes referred to as a develop inspect critical dimension (DICD).

More particularly, in one illustrative embodiment, modern photolithography processes generally involve the steps of: (1) applying a layer of photoresist above a wafer, typically accomplished by a spin-coating process; (2) pre-baking (or soft-baking) the layer of photoresist at a temperature of approximately 90–120° C. to reduce the level of solvents in the layer of photoresist and to improve the adhesion characteristics of the photoresist; (3) performing an exposure process, wherein a pattern is projected onto the layer of photoresist through a reticle used in a stepper tool to create a latent image in the layer of photoresist; (4) performing a post-exposure bake on the layer of photoresist at a temperature approximately 5–15° C. higher than the pre-bake process; (5) performing a develop process to turn the latent image in the layer of photoresist into the final resist image;

and (6) performing a post-bake process (or hard-bake) at a temperature of approximately 125–160° C. to remove residual solids, improve adhesion, and to increase the etch resistance of the photoresist. These process steps are well known to those skilled in the art and, thus, will not be described herein in any greater detail.

It is very important that all aspects of the stepper exposure tool be maintained in good working order. Slight variations in the performance of capabilities of the stepper exposure process and tool can adversely affect device performance. Moreover, it is important to detect when one or more aspects of the stepper exposure tool have degraded or are in the process of degrading so that appropriate maintenance activities may be performed and/or appropriate manufacturing decisions may be made.

The present invention is directed to a method and system that may solve, or at least reduce, some or all of the aforementioned problems.

SUMMARY OF THE INVENTION

The present invention is generally directed to methods of stepper exposure processes and tools, and system for accomplishing same. In one illustrative embodiment, the method comprises forming a grating structure comprised of a plurality of photoresist features above a semiconducting substrate, measuring at least one characteristic of at least one of the photoresist features at a plurality of locations within the grating structure, and determining if the measured characteristic of the photoresist features varies across the grating structure. In further embodiments, the method comprises indicating an error condition exists in the stepper exposure tool used to form the grating structure if the determined variance is not within acceptable limits. In even further embodiments, the method involves adjusting at least one parameter of a stepper exposure process to be performed on a subsequently processed wafer if the determined variance is not within acceptable limits.

BRIEF DESCRIPTION OF THE DRAWINGS

The invention may be understood by reference to the following description taken in conjunction with the accompanying drawings, in which like reference numerals identify like elements, and in which.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit aid scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

The present invention will now be described with reference to the attached figures. Although the various regions and structures of a semiconductor device are depicted in the drawings as having very precise, sharp configurations and profiles, those skilled in the art recognize that, in reality, these regions and structures are not as precise as indicated in the drawings. Additionally, the relative sizes of the various features and doped regions depicted in the drawings may be exaggerated or reduced as compared to the size of those features or regions on fabricated devices. Nevertheless, the attached drawings are included to describe and explain illustrative examples of the present invention. The words and phrases used herein should be understood and interpreted to have a meaning consistent with the understanding of those words and phrases by those skilled in the relevant art. No special definition of a term or phrase, i.e., a definition that is different from the ordinary and customary meaning as understood by those skilled in the art, is intended to be implied by consistent usage of the term or phrase herein. To the extent that a term or phrase is intended to have a special meaning, i.e., a meaning other than that understood by skilled artisans, such a special definition will be expressly set forth in the specification in a definitional manner that directly and unequivocally provides the special definition for the term or phrase.

In general, the present invention is directed to various methods of calibrating and controlling stepper exposure processes and tools, and system for accomplishing same. As will be readily apparent to those skilled in the art upon a complete reading of the present application, the present method is applicable to a variety of technologies, e.g., NMOS, PMOS, CMOS, etc., and it is readily applicable to a variety of devices, including, but not limited to, logic devices, memory devices, etc.

Semiconductor manufacturing generally involves multiple processes whereby multiple layers of material are formed above a semiconducting substrate, and portions of those layers are selectively removed using known photolithography and etching techniques until such time as a completed device is formed. Photolithography generally involves forming a patterned layer of photoresist material (positive or negative) above one or more layers of material that are desired to be patterned. Thereafter, the patterned photoresist layer is used as a mask in subsequent etching processes.

More particularly, the pattern desired to be formed in the underlying layer or layers of material is initially formed on a reticle. Thereafter, using an appropriate stepper tool, the image on the reticle is transferred to the layer of photoresist. Then, the layer of photoresist is developed so as to leave in place a patterned layer of photoresist substantially corresponding to the pattern on the reticle. This patterned layer of photoresist is then used as a mask in subsequent etching processes, wet or dry, performed on the underlying layer or layers of material, e.g., a layer of polysilicon, metal or insulating material, to transfer the desired pattern to the underlying layer. The patterned layer of photoresist is comprised of a plurality of photoresist features, e.g., line-type features or opening-type features, that are to be replicated in an underlying process layer.

Figure 2:
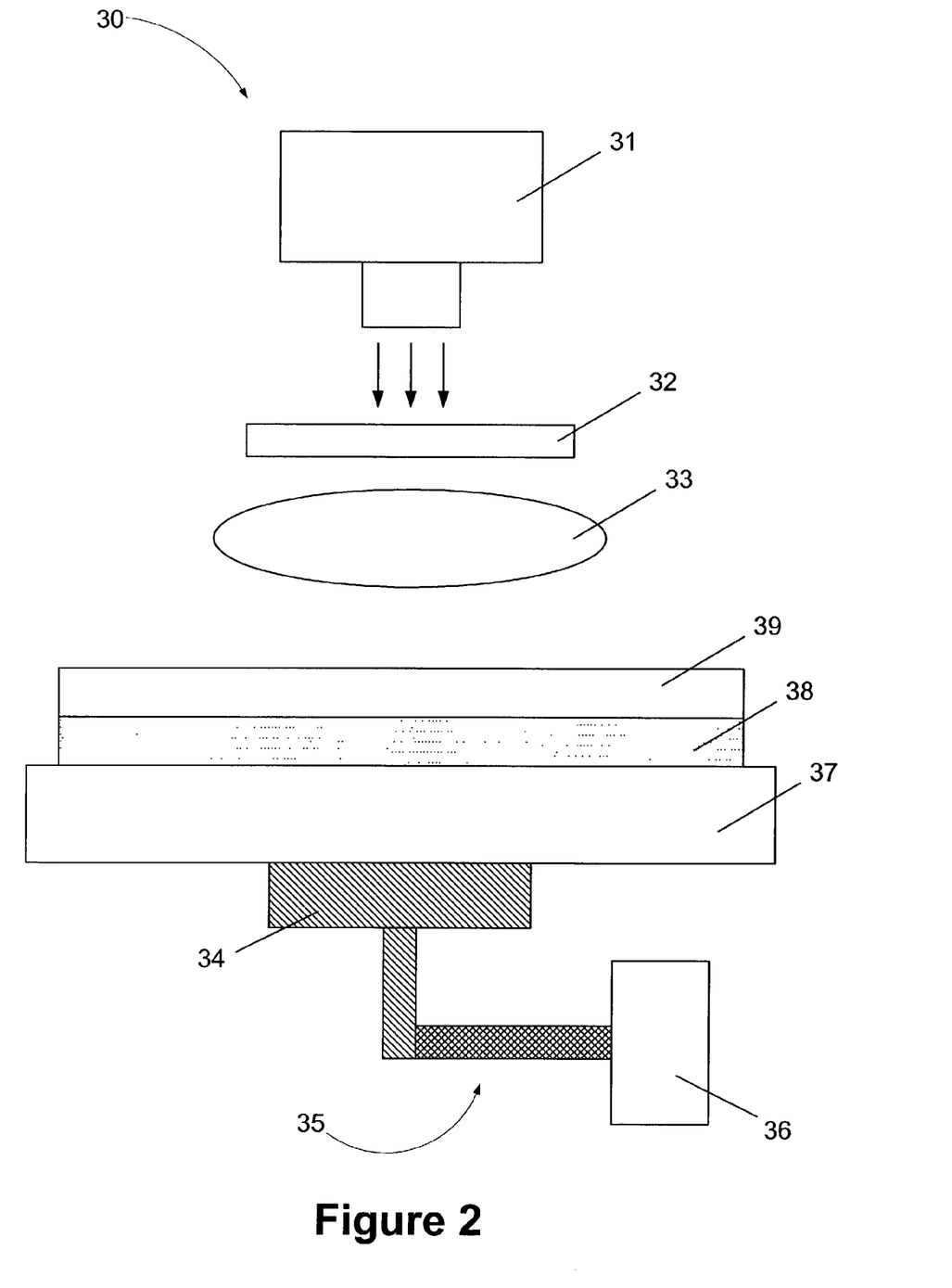
FIG. 2 is a schematic side view of portions of an illustrative stepper exposure tool.

FIG. 2 is a schematic side view of an illustrative stepper exposure tool 30 that may be employed with the present invention. In general, the stepper exposure tool 30 is comprised of a light source 31, a reticle 32, a reduction lens 33 and a wafer stage 34. The wafer stage 34 is operatively coupled to a positioning mechanism 35 comprised of an actuator 36, such as an electric motor. A wafer 37 having a layer of material 38, e.g., an insulating material, polysilicon, a metal, etc., and a layer of photoresist 39 (positive or negative type) formed thereabove, is positioned on the wafer stage 34. In general, light from the light source 31 will be used in projecting a pattern formed on the reticle 32 onto the layer of photoresist 39 to thereby render portions of the layer of photoresist less soluble (for a positive photoresist material). A development process will then be performed to remove the less soluble portions of the layer of photoresist 39 to thereby result in a patterned layer of photoresist comprised of a plurality of photoresist features. One or more etching process may then be performed to pattern the underlying layer of material 38 using the patterned layer of photoresist as a mask layer during the etching process.

Figure 3:
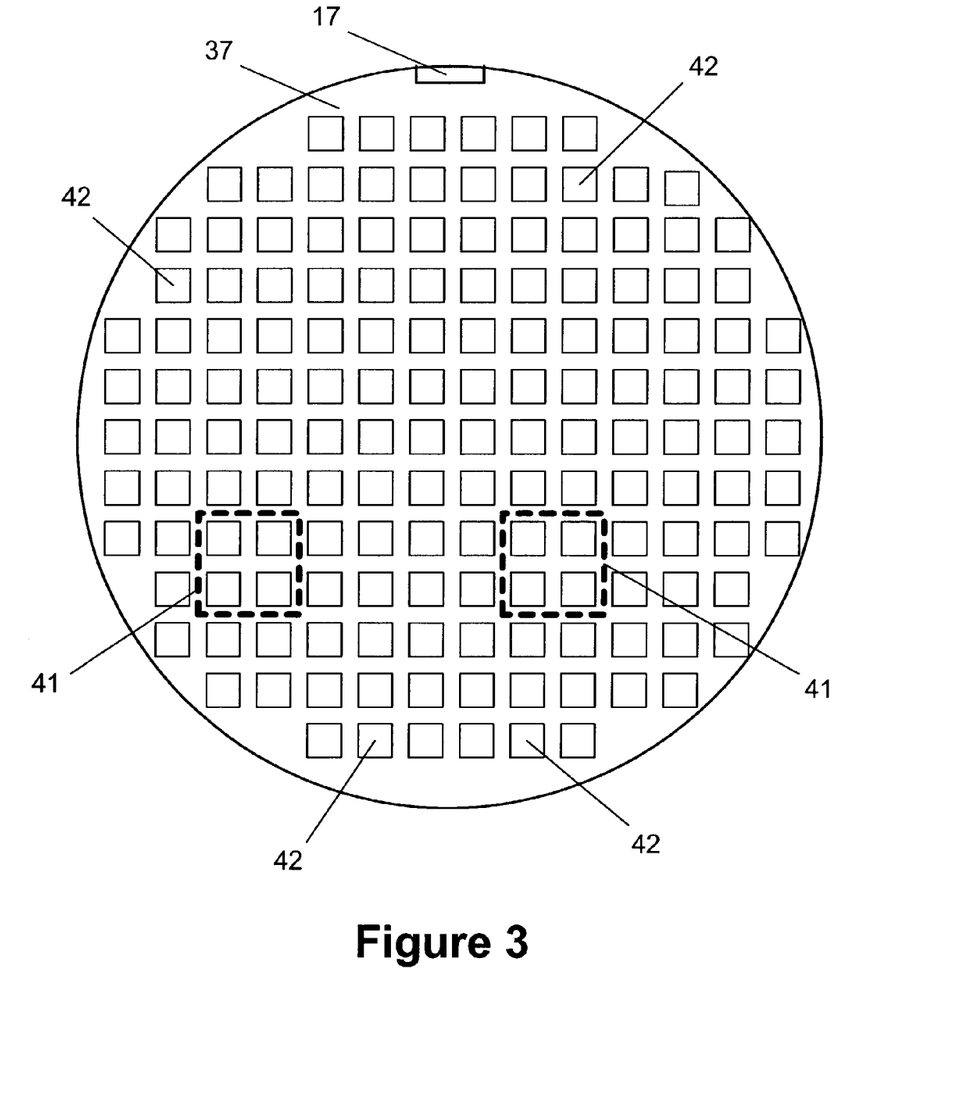
FIG. 3 is a plan view of an illustrative wafer depicting several production die.

As shown in FIG. 3, a plurality of production die 42 are formed above the wafer 37. The die 42 define an area of the wafer 37 where production integrated circuit devices, e.g., microprocessors, ASICs, memory devices, etc., will be formed. The size, shape and number of die 42 per wafer 37 depend upon the type of device under construction. For example, several hundred die 42 may be formed above an 8-inch diameter wafer 37. The wafer 37 may also have an alignment notch 17 that is used to provide relatively rough alignment of the wafer 37 prior to performing certain processes, e.g., an exposure process in a stepper tool.

Ultimately, the image on the reticle 32 will be transferred to the layer of photoresist 39, and the underlying process layer 38 will be patterned using the patterned layer of photoresist 39 as a mask during one or more subsequent etching processes. The exposure process performed on the wafer 37 is typically performed on a flash-by-flash basis as the wafer 37 is moved, or stepped, relative to the light source 31 within the stepper tool 30. During each step, the light source 31 projects light onto a given area of the wafer 37, i.e., each flash is projected onto an exposure field 41 (indicated by dashed lines). The size of the exposure field 41, as well as the number of die 42 within each exposure field 41, may vary greatly. For example, an illustrative exposure field 41 is depicted in FIG. 3 wherein four of the die 42 fall within the exposure field 41, i.e., a so-called 2×2 pattern. However, the number of die 42 and size of the exposure field 41 may vary. For example, integrated circuits may be exposed using a 1×2 pattern (covering 2 die), a 5×5 pattern (covering 25 die), etc. The precise pattern of the exposure field 41 may be based upon the product under construction as well as the desires and judgment of the appropriate process engineer.

In general, the present invention involves forming one or more grating structures 60 (see FIGS. 4A–4C) in the layer of photoresist 39 and subjecting the grating structures 60 to one or more scatterometric measurement processes. Based upon the results of these measurements, a variety of information may be obtained as to the effectiveness of the exposure process and the condition of one or more components of the stepper exposure tool 30. Additionally, various control actions may be taken based upon these measurements.

The present invention may be employed with any type of exposure tool useful for exposing a layer of photoresist, or other like material. In one illustrative embodiment, the exposure tool 30 is a Model No. 5500/300 manufactured by ASML. Of course, as will be understood by those skilled in the art, the schematic depiction of the exposure tool 30 in FIG. 2 is very simplified. An actual stepper tool 30 may include many additional features, such as one or more focusing lenses, one or more light filters, a laser light source or a mercury arc lamp for exposure purposes and various mechanical systems and mechanisms for moving the wafer stage, etc.

Figure 4A:
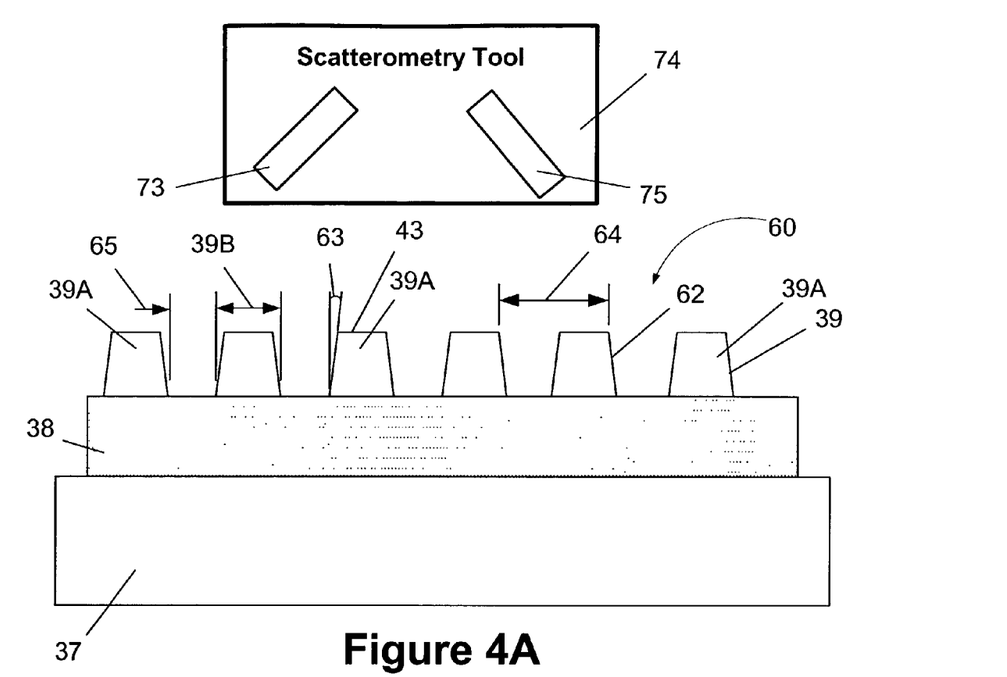
FIGS. 4A–4C depicts an illustrative grating surface formed above a semiconducting substrate.

Some aspects of the present invention will now be described with reference to FIGS. 4A–4C. According to one embodiment of the present invention, a grating structure 60 is comprised of a plurality of photoresist features 39A. The grating structure 60 may be of any size of configuration. Typically, the grating structure 60 will be relatively large, e.g., up to, for example, 1000 $\mu m \times 1000$ $\mu m$ (1,000,000 $\mu m^2$). Of course, the grating structure 60 need not be square or even rectangular in configuration.

The number of photoresist features 39A that comprise the grating structure 60, as well as the cross-sectional configuration of the photoresist features 39A and the pitch 64 and/or spacing 65 therebetween, may also vary. For example, as shown in FIG. 4A, the photoresist features 39A have a generally trapezoidal cross-sectional configuration. The illustrative photoresist features 39A may be a plurality of line-type photoresist features 39A used as a mask in forming gate electrode structures for a semiconductor device.

Figure 4B:
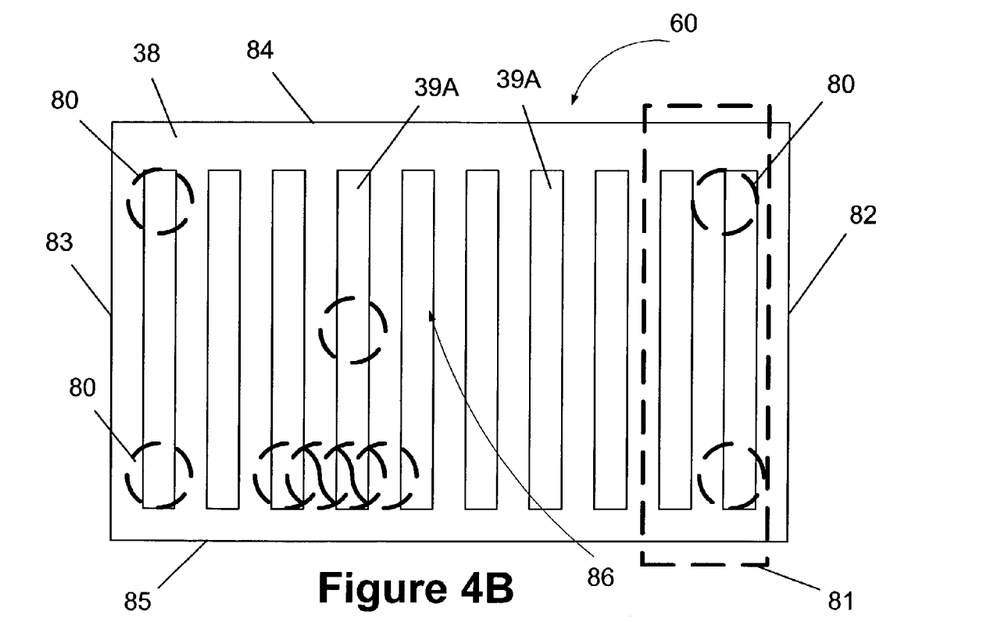
Figure 4C:
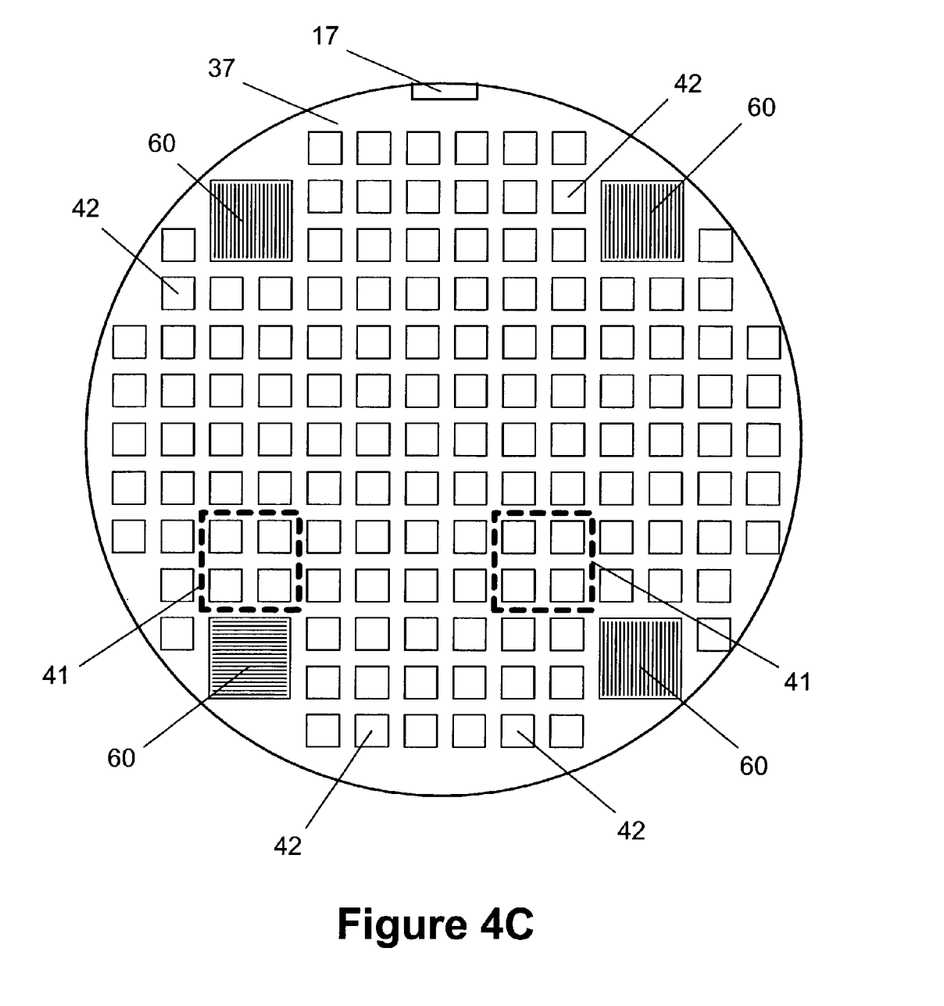

As indicated in FIG. 4C, one or more of the grating structures 60 may be formed above a wafer 37. The number and location of the grating structures 60 may be varied based upon the judgment of the responsible process engineer. Depending upon the size of the grating structures 60, they may also be formed in the layer of photoresist 39 above the space between the die 42, i.e., in the area defined by so-called scribe lines.

In one embodiment, the pattern of the grating structure 60 occupies the entire useful area of the reticle. That is, the grating structure 60 is formed with an area defined by a single exposure field 41 of the stepper exposure process. This special reticle may be used to expose selected areas of the layer of photoresist 39 either before or after exposure processes have been performed on the production die 42 of the wafer 37. However, it is not required that the grating structure 60 occupy the entirety of a single flash field 41 of the stepper exposure process. Thus, the exact reticle design used in forming the grating structure 60 may be varied depending upon the application.

The grating structure 60 may be formed as a separate test structure, or in some embodiments, it may be comprised of photoresist features 39A, e.g., lines, that are used to form actual production devices. For example, the grating structure 60 may be essentially a test structure that is formed in an area defined by an unused area on a scribe line of a wafer. In the case of actual production devices, the photoresist features 39A that comprise the grating structure 60 may be formed as part of the processes of forming floating gates or control gates as part of a flash memory array. The photoresist features 39A that are part of the grating structure 60 may be formed at the same time that similar photoresist features 39A are being formed for production devices formed on the wafer 37. That is, a pattern for the grating structure 60 may be formed in a reticle that will be used in the process of exposing the layer of photoresist 39 to form production integrated circuit devices within the die 42. Alternatively, a special reticle may be used wherein a single grating structure 60 occupies the entirety of the reticle. This separate reticle may be used before or after the reticle used to expose the production devices is used.

As stated previously, one or more locations or regions 80 (see FIG. 4B) on the grating structure 60 may be measured using scatterometric techniques. An illustrative scatterometry tool 74 that may be used with the present invention is comprised of a representative light source 73 and a detector 75 depicted in FIG. 4A. Ultimately, the grating structure(s) 60 will be measured using scatterometric techniques, and these measurements will be used for purposes described more fully below. The scatterometry measurements of the grating structure 60 may be performed after the layer of photoresist 39 has been subjected to a post-exposure bake process, but prior to the layer of photoresist 39 being subjected to a development process. Alternatively, the scatterometry measurements may be taken after the layer of photoresist 39 has been subjected to a development process.

A variety of scatterometry tools 74 may be used with the present invention, e.g., so-called 20-type systems and lens-type scatterometry tools. The scatterometry tool 74 may use white light, or some other wavelength or combination of wavelengths, depending on the specific implementation. Typically, the scatterometry tool 74 will generate an incident beam that has a wide spectral composition and wherein the intensity of the light changes slowly in comparison to changes in wavelength. The angle of incidence of the light may also vary, depending on the specific implementation. The optical characteristic traces generated by the scatterometry tool 74 may be based upon a comparison of light intensity to wavelength (for white light, fixed angle type scatterometry tools) or a comparison of intensity to incident angle (for angle resolved systems that use a single light source).

As shown in FIG. 4B, scatterometric measurements may be made at a plurality of regions 80 on the grating structure 60. The size of the regions 80 or spots will vary depending upon the particular scatterometry tool 74 employed. For example, the measured regions 80 may have a diameter of approximately 40–70 $\mu$m. Of course, the size and shape of the scatterometry measurement field may vary depending upon the particular scatterometry tool employed.

The number of regions 80 of the grating structure 60 that are measured, as well as the location of those measurements within the grating structure 60, may vary depending upon the particular application. In one illustrative embodiment, a plurality of regions 80 are measured across the area of the grating structure 60 to determine localized variations within a particular grating structure 60. For example, one or more regions 80 may be measured in an area near each corner of the grating structure 60. Additionally, a number of regions 80 may be measured in which the measured sites overlap one another to some degree, as shown in FIG. 4B. The number of regions 80 measured on each grating structure 60 may also vary. For example, 70–150 regions may be measured on an illustrative grating structure 60 having dimensions of approximately 500 $\mu$m×500 $\mu$m.

The scatterometric measurements described herein may be used, in one embodiment, to determine variations of the photoresist features 39A across a given grating structure 60. Such variations may include, but should not be considered as limited to, variations in the critical dimension or cross-sectional profile of one or more of the photoresist features 39A within the grating structure 60.

Such variations may be used for a variety of purposes. In one embodiment, such methodologies may be employed to qualify, check or confirm various operational characteristics of the stepper exposure tool 30 and/or the stepper exposure process. For example, if the scatterometric measurements indicate variations in the critical dimension and/or profile of the photoresist features 39A in an area 81 adjacent the end 82 of the grating structure 60, then this may be indicative of a defect or potential problems with one or more operational aspects or components of the stepper exposure tool 30. For example, such metrology results may be indicative of a faulty or defective lens 33 or a fault in the positioning of the wafer 37 by the wafer transport mechanism 35. In response, an error condition may be indicated and maintenance activities may be performed to correct such problems. In such cases, an error condition may be indicated if the measured variations exceed a preselected limit or are not within established allowable limits. In general, the present invention may be used to detect lens distortions or defects, light source (laser or mercury lamp) non-uniformities and/or variations in a reticle. In some cases, identifying the error associated with a reticle (if any) and an error associated with another component of the stepper tool (if any), e.g., a lens defect, may involve additional analysis.

Alternatively, the particular stepper exposure tool 30 may be limited to use with less critical parts. As another example, variations in the critical dimension of the photoresist features 39A may show a size variation pattern wherein the critical dimensions 39B of the photoresist features 39A decrease in size as one moves from the edge 82 to the edge 83. Such metrology data may be indicative of variations in the focal plane of the stepper across the area defined by the grating structure 60. Such a focal plan variation may be due to one or more aspects of the optical components of the stepper exposure tool 30 or it may be due to problems with the wafer stage 34 and/or positioning system 35. Additionally, the scatterometric measurements may be used to determine if there is a variation in the measured characteristics of the photoresist features from an edge region 82, 83, 84 or 85 to a center region 86 of the grating structure 60.

As set forth previously, one or more of the grating structures 60 may be formed above the wafer 37. In such a situation, additional data may be obtained as to various across-wafer characteristics which may enable more sophisticated analyses as to actual or potential problems with the stepper exposure tool 30 and/or the stepper exposure process. More particularly, as shown in FIG. 4C, four illustrative grating structures 60 are formed above the wafer 37. Of course, the number and location of the multiple grating structures 60 may be varied.

The present invention may also be used in the context of compensating for the deficiencies found as a result of the scatterometric measurements. For example, if the measurement of a grating structure 60 indicates a deviation in the critical dimension 39B of the photoresist features 39A from the edge 82 of the grating structure 60 to the edge 83, the wafer stage 34 and/or wafer positioning mechanism 35 may be repositioned in an effort to insure that this undesirable tilt does not occur on subsequent wafers. Alternatively, one or more optical components of the stepper exposure tool 30 may be adjusted to compensate for this situation. For example, adjustments could be made to one or more of the optical lenses, the exposure light source, various optical filters and to the positioning of the wafer within the stepper exposure tool.

Through use of the scatterometry tool 74, an optical characteristic trace for each measurement region 80 is generated. The optical characteristic trace may then be compared to a reference trace in, for example, a library of such traces to determine the characteristics of the photoresist features 39A under consideration, e.g., critical dimension, cross-sectional profile, sidewall angle, etc. Scatterometry-based measurement techniques are well known to those skilled in the art and will not be described herein in any further detail.

Figure 5:
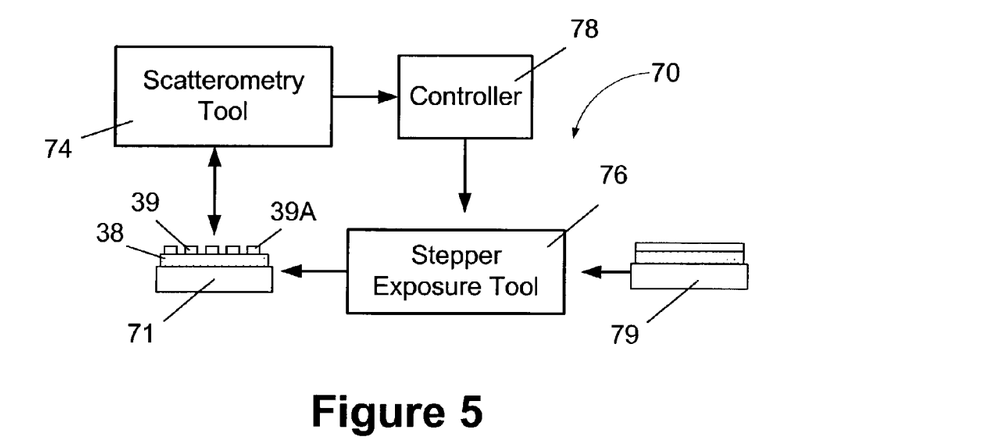
FIG. 5 depicts an illustrative embodiment of a system in accordance with one embodiment of the present invention.

An illustrative system 70 that may be used in one embodiment of the present invention is shown in FIG. 5. The system 70 is comprised of a scatterometry tool 74, a stepper exposure tool 76, and a controller 78. As indicated in FIG. 5, the wafer 71 is representative of one or more wafers having a film stack comprised of at least one process layer 38 and a patterned layer of photoresist 39 formed thereabove. The wafer 71 is depicted at the point in the process wherein it has previously been processed in the stepper exposure tool 76. The layer of photoresist 39 on the wafer 71 was subjected to an exposure process in the stepper tool 76 to transfer the features 39A defined in the reticle (not shown) to the layer of photoresist 39. During this process, the grating structures 60 were defined in the layer of photoresist 39, as were many other photoresist features that will be used to ultimately form corresponding features in the underlying process layer 38. Thereafter, a post-exposure bake process may be performed on the layer of photoresist 39. Ultimately, the layer of photoresist 39 will be subjected to a development process whereby soluble portions of the layer of photoresist 39 will be removed. This will result in the definition of a patterned layer of photoresist 39 that reflects the pattern in the reticle used during the exposure process. This patterned layer of photoresist 39 will be used in patterning the underlying process layer by performing one or more known etching processes.

Control equations may be employed to adjust the operating recipe of the photolithography tool 76 in situations where the methods described herein indicate that an adjustment is warranted. The control equations may be developed empirically using commonly known linear or non-linear techniques. The controller 78 may automatically control the operating recipes of the photolithography tool 76 used to form a layer of photoresist on the subsequently processed wafers 79. Through use of the present invention, the extent and magnitude of variations in thicknesses of layers of photoresist may be reduced.

In the illustrated embodiments, the controller 78 is a computer programmed with software to implement the functions described herein. Moreover, the functions described for the controller 78 may be performed by one or more controllers spread through the system. For example, the controller 78 may be a fab level controller that is used to control processing operations throughout all or a portion of a semiconductor manufacturing facility. Alternatively, the controller 78 may be a lower level computer that controls only portions or cells of the manufacturing facility. Moreover, the controller 78 may be a stand-alone device, or it may reside on the scatterometry tool 74 or on the stepper exposure tool 76. However, as will be appreciated by those of ordinary skill in the art, a hardware controller (not shown) designed to implement the particular functions may also be used.

Portions of the invention and corresponding detailed description are presented in terms of software, or algorithms and symbolic representations of operations on data bits within a computer memory. These descriptions and representations are the ones by which those of ordinary skill in the art effectively convey the substance of their work to others of ordinary skill in the art. An algorithm, as the term is used here, and as it is used generally, is conceived to be a self-consistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be understood, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" or "displaying" or the like, refer to the actions and processes of a computer system, or similar electronic computing device, that manipulates and transforms data represented as physical, electronic quantities within the computer system's registers and memories into other data similarly represented as physical quantities within the computer system memories or registers or other such information storage, transmission or display devices.

An exemplary software system capable of being adapted to perform the functions of the controller 78, as described, is the Catalyst system offered by KLA Tencor, Inc. The Catalyst system uses Semiconductor Equipment and Materials International (SEMI) Computer Integrated Manufacturing (CIM) Framework compliant system technologies, and is based on the Advanced Process Control (APC) Framework. CIM (SEMI E81-0699-Provisional Specification for CIM Framework Domain Architecture) and APC (SEMI E93-0999-Provisional Specification for CIM Framework Advanced Process Control Component) specifications are publicly available from SEMI.

The present invention is directed to various methods of stepper exposure processes and tools, and system for accomplishing same. In one illustrative embodiment, the method comprises forming a grating structure comprised of a plurality of photoresist features above a semiconducting substrate, measuring at least one characteristic of at least one of the photoresist features at a plurality of locations within the grating structure, and determining if the measured characteristic of the photoresist features varies across the grating structure. In further embodiments, the method comprises indicating an error condition exists in the stepper exposure tool used to form the grating structure if the determined variance is not within acceptable limits. In even further embodiments, the method involves adjusting at least one parameter of a stepper exposure process to be performed on a subsequently processed wafer if the determined variance is not within acceptable limits.

In one embodiment, the system is comprised of a stepper exposure tool used in forming a grating structure comprised of a plurality of photoresist features above a semiconducting substrate, a scatterometry tool for measuring at least one characteristic of at least one of the photoresist features at a plurality of locations within the grating structure, and a controller for determining if the measured characteristic of the photoresist features varies across the grating structures.

Through use of the present invention, better process control may be achieved in modern integrated circuit manufacturing facilities. Additionally, the present invention may enable more precise formation of gate electrode structures of transistors employed in integrated circuit devices, thereby improving device performance and increasing production yields.

The particular embodiments disclosed above are illustrative only, as the invention may be modified and practiced in different but equivalent manners apparent to those skilled in the art having the benefit of the teachings herein. For example, the process steps set forth above may be performed in a different order. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A method, comprising:
    forming a grating structure comprised of a plurality of photoresist features above a semiconducting substrate;
    measuring at least one characteristic of at least one of said photoresist features at a plurality of locations within said grating structure; and
    determining if said measured characteristic of said photoresist features varies from a first edge of said grating structure to a second edge of said grating structure.

2. The method of claim 1, wherein forming said grating structure comprised of a plurality of photoresist features comprises forming said grating structure comprised of a plurality of line-type photoresist features.

3. The method of claim 1, wherein said semiconducting substrate is comprised of silicon.

4. The method of claim 1, wherein measuring at least one characteristic of at least one of said plurality of photoresist features comprises measuring at least one of a critical dimension, a cross-sectional profile, and a sidewall angle of at least one of said plurality of photoresist features.

5. The method of claim 1, further comprising determining if said measured characteristic of said photoresist features varies from an edge region of said grating structure to a center region of said grating structure.

6. The method of claim 1, further comprising indicating an error condition exists in a stepper exposure tool used in forming said plurality of photoresist features.

7. The method of claim 1, further comprising indicating an error condition exists in a stepper exposure tool used in forming said plurality of photoresist features if said determined variance exceeds a preselected limit.

8. The method of claim 1, further comprising indicating an error condition exists in a stepper exposure tool used in forming said plurality of photoresist features if said determined variance is not within acceptable limits.

9. The method of claim 1, further comprising adjusting at least one parameter of a stepper exposure process to be performed on a subsequently processed substrate if said determined variance is not within acceptable limits.

10. The method of claim 9, wherein adjusting at least one parameter of a stepper exposure process comprises adjusting at least one of a focal plane location, a position of said substrate, a tilt of said substrate and an intensity of a light source.

11. The method of claim 1, further comprising limiting use of a stepper exposure tool used to form said photoresist features if said determined variance exceeds a preselected allowable limit.

12. The method of claim 11, wherein limiting the use of said stepper exposure tool comprises prohibiting the use of said stepper exposure tool in certain situations.

13. The method of claim 1, wherein forming said grating structure comprised of a plurality of photoresist features above said semiconducting substrate comprises forming a plurality of grating structures above said semiconducting substrate, each of said grating structures being comprised of a plurality of photoresist features.

14. The method of claim 13, further comprising measuring at least one characteristic of at least one of said photoresist features at a plurality of locations within each of said plurality of grating structures.

15. A method, comprising:
    forming a grating structure comprised of a plurality of photoresist features above a semiconducting substrate;
    measuring at least one characteristic of at least one of said photoresist features at a plurality of locations within said grating structure;
    determining if said measured characteristic of said photoresist features varies from a first edge of said grating structure to a second edge of said grating structure; and
    indicating an error condition exists in a stepper exposure tool used in forming said plurality of photoresist features if said determined variance is not within acceptable limits.

16. The method of claim 15, wherein forming said grating structure comprised of a plurality of photoresist features comprises forming said grating structure comprised of a plurality of line-type photoresist features.

17. The method of claim 15, wherein said semiconducting substrate is comprised of silicon.

18. The method of claim 15, wherein measuring at least one characteristic of at least one of said plurality of photoresist features comprises measuring at least one of a critical dimension, a cross-sectional profile, and a sidewall angle of at least one of said plurality of photoresist features.

19. The method of claim 15, further comprising determining if said measured characteristic of said photoresist features varies from an edge region of said grating structure to a center region of said grating structure.

20. The method of claim 15, further comprising adjusting at least one parameter of a stepper exposure process to be performed on a subsequently processed substrate if said determined variance is not within acceptable limits.

21. The method of claim 20, wherein adjusting at least one parameter of a stepper exposure process comprises adjusting at least one of a focal plane location, a position of said substrate, a tilt of said substrate and an intensity of a light source.

22. The method of claim 15, further comprising limiting use of a stepper exposure tool used to form said photoresist features if said determined variance is not within allowable limits.

23. The method of claim 22, wherein limiting the use of said stepper exposure tool comprises prohibiting the use of said stepper exposure tool in certain situations.

24. The method of claim 15, wherein forming said grating structure comprised of a plurality of photoresist features above said semiconducting substrate comprises forming a plurality of grating structures above said semiconducting substrate, each of said grating structures being comprised of a plurality of photoresist features.

25. The method of claim 24, further comprising measuring at least one characteristic of at least one of said photoresist features at a plurality of locations within each of said plurality of grating structures.

26. A method, comprising:
forming a grating structure comprised of a plurality of photoresist features above a semiconducting substrate;
measuring at least one characteristic of at least one of said photoresist features at a plurality of locations within said grating structure;
determining if said measured characteristic of said photoresist features varies from a first edge of said grating structure to a second edge of said grating structure; and
adjusting at least one parameter of a stepper exposure process to be performed on a subsequently processed substrate if said determined variance is not within acceptable limits.

27. The method of claim 26, wherein forming said grating structure comprised of a plurality of photoresist features comprises forming said grating structure comprised of a plurality of line-type photoresist features.

28. The method of claim 26, wherein said semiconducting substrate is comprised of silicon.

29. The method of claim 26, wherein measuring at least one characteristic of at least one of said plurality of photoresist features comprises measuring at least one of a critical dimension, a cross-sectional profile, and a sidewall angle of at least one of said plurality of photoresist features.

30. The method of claim 26, further comprising determining if said measured characteristic of said photoresist features varies from an edge region of said grating structure to a center region of said grating structure.

31. The method of claim 26, further comprising indicating an error condition exists in a stepper exposure tool used in forming said plurality of photoresist features if said determined variance is not within acceptable limits.

32. The method of claim 26, wherein adjusting at least one parameter of a stepper exposure process comprises adjusting at least one of a focal plane location, a position of said substrate, a tilt of said substrate and an intensity of a light source.

33. The method of claim 26, wherein forming said grating structure comprised of a plurality of photoresist features above said semiconducting substrate comprises forming a plurality of grating structures above said semiconducting substrate, each of said grating structures being comprised of a plurality of photoresist features.

34. The method of claim 33, wherein limiting the use of said stepper exposure tool comprises prohibiting the use of said stepper exposure tool in certain situations.

35. The method of claim 26, further comprising limiting use of a stepper exposure tool used to form said photoresist features if said determined variance exceeds a preselected allowable limit.

36. The method of claim 35, further comprising measuring at least one characteristic of at least one of said photoresist features at a plurality of locations within each of said plurality of grating structures.

37. A method, comprising:
forming a grating structure comprised of a plurality of photoresist features above a semiconducting substrate;
measuring at least one characteristic of at least one of said photoresist features at a plurality of locations within said grating structure;
determining if said measured characteristic of said photoresist features varies from a first edge of said grating structure to a second edge of said grating structure; and
limiting use of a stepper exposure tool used to form said photoresist features if said determined variance exceeds a preselected allowable limit.

38. The method of claim 37, wherein forming said grating structure comprised of a plurality of photoresist features comprises forming said grating structure comprised of a plurality of line-type photoresist features.

39. The method of claim 37, wherein said semiconducting substrate is comprised of silicon.

40. The method of claim 37, wherein measuring at least one characteristic of at least one of said plurality of photoresist features comprises measuring at least one of a critical dimension, a cross-sectional profile, and a sidewall angle of at least one of said plurality of photoresist features.

41. The method of claim 37, further comprising determining if said measured characteristic of said photoresist features varies from an edge region of said grating structure to a center region of said grating structure.

42. The method of claim 37, further comprising indicating an error condition exists in a stepper exposure tool used in forming said plurality of photoresist features if said determined variance is not within acceptable limits.

43. The method of claim 37, further comprising adjusting at least one parameter of a stepper exposure process to be performed on a subsequently processed substrate if said determined variance is not within acceptable limits.

44. The method of claim 43, wherein adjusting at least one parameter of a stepper exposure process comprises adjusting at least one of a focal plane location, a position of said substrate, a tilt of said substrate and an intensity of a light source.

45. The method of claim 37, wherein limiting the use of said stepper exposure tool comprises prohibiting the use of said stepper exposure tool in certain situations.

46. The method of claim 37, wherein forming said grating structure comprised of a plurality of photoresist features above said semiconducting substrate comprises forming a plurality of grating structures above said semiconducting substrate, each of said grating structures being comprised of a plurality of photoresist features.

47. The method of claim 46, further comprising measuring at least one characteristic of at least one of said photoresist features at a plurality of locations within each of said plurality of grating structures.

48. A method, comprising:
forming a grating structure comprised of a plurality of photoresist features above a semiconducting substrate;
measuring at least one characteristic of at least one of said photoresist features at a plurality of locations within said grating structure; and
determining if said measured characteristic of said photoresist features varies from an edge region of said grating structure to a center region of said grating structure.

49. A method, comprising:
forming a grating structure comprised of a plurality of photoresist features above a semiconducting substrate;
measuring at least one characteristic of at least one of said photoresist features at a plurality of locations within said grating structure;
determining if said measured characteristic of said photoresist features varies from an edge region of said grating structure to a center region of said grating structure; and indicating an error condition exists in a stepper exposure tool used in forming said plurality of photoresist features if said determined variance is not within acceptable limits.

50. A method, comprising:

forming a grating structure comprised of a plurality of photoresist features above a semiconducting substrate;

measuring at least one characteristic of at least one of said photoresist features at a plurality of locations within said grating structure;

determining if said measured characteristic of said photoresist features varies from an edge region of said grating structure to a center region of said grating structure; and adjusting at least one parameter of a stepper exposure process to be performed on a subsequently processed substrate if said determined variance is not within acceptable limits.

51. A method, comprising:

forming a grating structure comprised of a plurality of photoresist features above a semiconducting substrate;

measuring at least one characteristic of at least one of said photoresist features at a plurality of locations within said grating structure;

determining if said measured characteristic of said photoresist features varies from an edge region of said grating structure to a center region of said grating structure; and limiting use of a stepper exposure tool used to form said photoresist features if said determined variance exceeds a preselected allowable limit.

* * * * *

UNITED STATES PATENT AND TRADEMARK OFFICE
CERTIFICATE OF CORRECTION

PATENT NO.    : 6,972,853 B1
DATED         : December 6, 2005
INVENTOR(S)   : James Broc Stirton and Homi E. Nariman It is certified that error appears in the above-identified patent and that said Letters Patent is hereby corrected as shown below:

Column 13,
Line 48, delete "claim 33" and insert -- claim 35 --.

Signed and Sealed this

Seventh Day of February, 2006

JON W. DUDAS
*Director of the United States Patent and Trademark Office*